United States Patent [19]

Gross et al.

[11] Patent Number: 5,184,632
[45] Date of Patent: Feb. 9, 1993

[54] DENTAL FLOSSING DEVICE

[75] Inventors: Joseph Gross, Moshav Mazor; Shlomo Zucker, Mihmoret, both of Israel

[73] Assignee: Product Development (Z.G.S.) Ltd., Petach Tikva, Israel

[21] Appl. No.: 797,655

[22] Filed: Nov. 25, 1991

Related U.S. Application Data

[63] Continuation-in-part of Ser. No. 759,007, Sep. 12, 1991.

[30] Foreign Application Priority Data

Nov. 27, 1990 [IL] Israel .................................. 96490
May 5, 1991 [IL] Israel .................................. 98062

[51] Int. Cl.⁵ .............................................. A61C 15/00
[52] U.S. Cl. ...................................... 132/326; 132/323; 132/322
[58] Field of Search ............... 132/321, 322, 323, 324, 132/325, 326, 327

[56] References Cited

U.S. PATENT DOCUMENTS

| | | | |
|---|---|---|---|
| 4,014,354 | 3/1977 | Garrett | 132/322 |
| 4,235,253 | 11/1980 | Moore | 132/322 |
| 4,586,521 | 5/1986 | Urso | 132/322 |
| 4,605,025 | 8/1986 | McSpadden | 132/322 |
| 4,941,488 | 7/1990 | Marxer et al. | 132/323 |
| 5,016,660 | 5/1991 | Boggs | 132/322 |

*Primary Examiner*—Gene Mancene
*Assistant Examiner*—Cindy A. Cherichetti
*Attorney, Agent, or Firm*—Benjamin J. Barish

[57] ABSTRACT

A dental flossing device includes a housing manually grippable by a user, a pair of spaced arms projecting from one end of the housing for engaging the opposite ends of a length of dental floss to be tautly secured along a dental floss axis between the arms, and a drive for displacing the length of dental floss when secured between the arms. The drive displaces at least one end of the length of dental floss, when secured between the arms, through a unidirectional, curved closed-loop planar path defined by the two axes substantially perpendicular to each other and to the dental floss axis. In one described embodiment, only one end of the length of dental floss is displaced in the above-defined unidirectional, curved, closed-loop path; and in a second described embodiment, each of the two ends of the length of dental floss is displaced in the above-defined unidirectional, curved, closed-loop path.

19 Claims, 5 Drawing Sheets

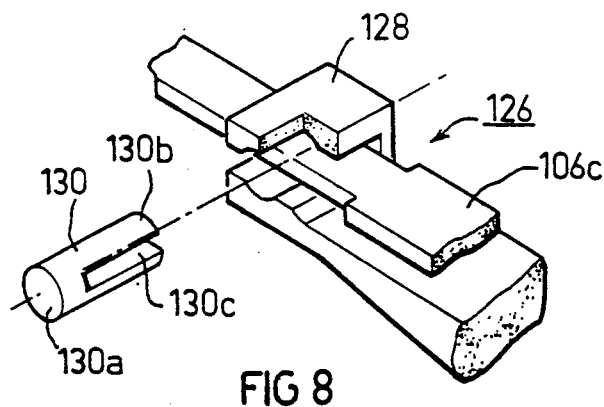
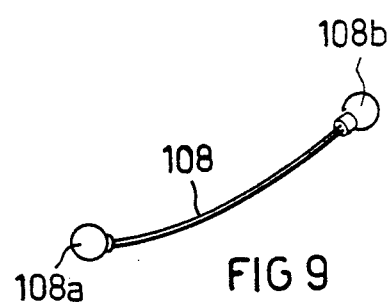
FIG 8
FIG 9
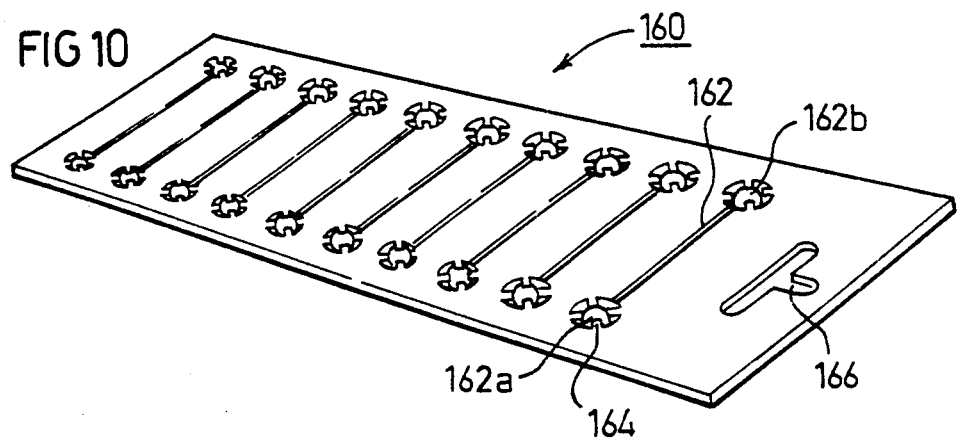
FIG 10
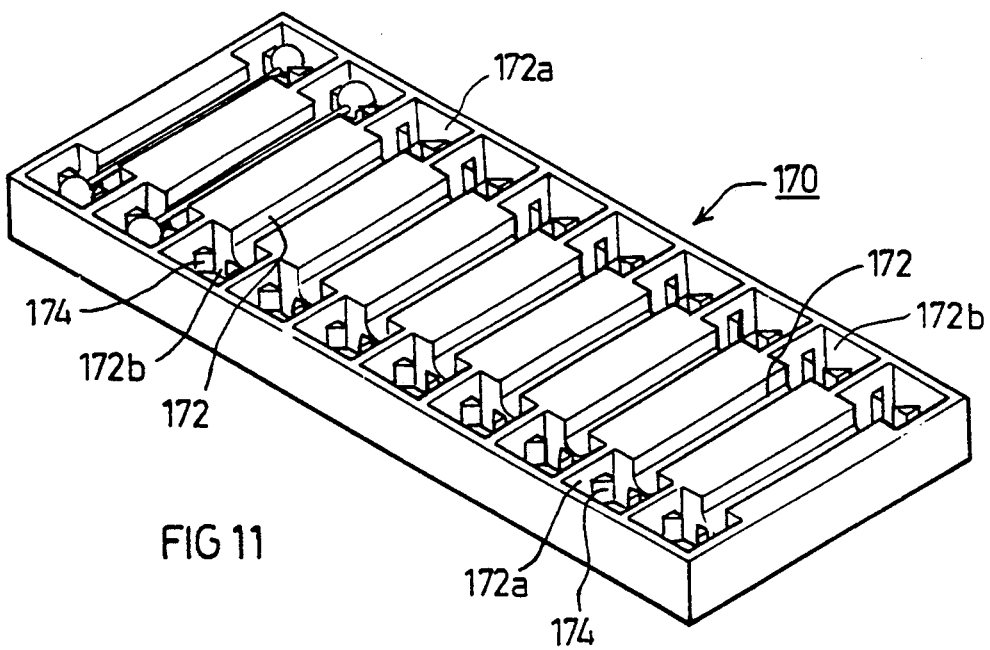
FIG 11

DENTAL FLOSSING DEVICE

RELATED APPLICATION

The present application is a continuation-in-part of our patent application Ser. No. 07/759,007 filed Sep. 12, 1991 pending.

FIELD AND BACKGROUND OF THE INVENTION

The present invention relates to dental flossing devices, and particularly to powered devices which include a drive for reciprocating or oscillating the dental floss.

Because of the difficulty and awkwardness of manually flossing teeth, a number of power flossing devices have been developed for reciprocating or oscillating the dental floss between the user's teeth. Examples of known power devices are described in our prior U.S. Pat. No. 5,033,150, as well as in U.S. Pat. Nos. 4,605,025, 4,458,702, 4,338,957, 4,307,740, 4,235,253 and 3,759,274. Generally speaking, the known devices reciprocate the dental floss either parallel to the axis of the dental floss, and/or perpendicular to the axis of the dental floss. However, it has been found that such flossing devices not only do not remove the deposits of dental plaque from between the teeth in the most effective manner, but also may damage the soft gingival tissue by the "saw-like" motion when reciprocated parallel to the dental floss axes.

OBJECTS AND BRIEF SUMMARY OF THE INVENTION

An object of the present invention is to provide dental flossing device having advantages in the above respects. Another object of the invention is to provide a dental flossing device which permits loading with floss in a quick and simple manner. A further object of the invention is to provide a dental flossing device consisting of a few simple parts which can be produced and assembled in volume and at relatively low cost.

According to the present invention, there is provided a dental flossing device comprising: a housing manually grippable by a user; a pair of spaced arms projecting from one end of the housing and including floss-engaging means for engaging the opposite ends of a length of dental floss to be tautly secured along a dental floss axis between the arms; and a drive within the housing for displacing the length of dental floss when secured between the arms; characterized in that the drive displaces at least one end of the length of dental floss, when secured between the arms, through a unidirectional, curved, closed-loop planar path defined by the two axes substantially perpendicular to each other and to the dental floss axis.

By thus displacing the dental floss through the defined unidirectional, curved, closed-loop path, the dental floss more effectively removes the dental plaque from between the teeth. Moreover, since the dental floss is not reciprocated parallel to its longitudinal axis, it does not produce a "saw-like motion" which may damage the soft gingival tissue.

In one described embodiment of the invention, only one end of the length of dental, floss is displaced in the above-defined unidirectional, curved, closed-loop path. According to a second described embodiment, both ends of the length of dental floss are displaced in the above-defined circular path.

According to further features in the latter described embodiment, both of the arms are part of a fork, which fork is displaced by the drive through the circular path.

According to further features in the latter described embodiment, the pair of arms are yieldable and include edge slots at their outer tips to permit a precut length of dental floss having enlargements at its opposite ends to be quickly applied to the outer tips of the arms by forcing the outer tips of the arms towards each other while inserting the precut length of dental floss through the edge slots.

According to still further features in the latter described embodiment, the outer tips of the arms are also formed with cam surfaces cooperable with surfaces formed in a holder for the precut length of dental floss, for forcing the outer tips of the arms towards each other when applying a precut length of dental floss thereto. Such a construction greatly facilitates the application and removal of dental floss units.

Further features and advantages of the invention will be apparent from the description below.

BRIEF DESCRIPTION OF THE DRAWINGS

The invention is herein described, by way of example only, with reference to the accompanying drawings, wherein:

FIG. 5 is a perspective view more particularly illustrating the internal construction of the device of FIG. 4;

FIG. 5a illustrates the planar circular path transvered by both ends of the dental floss in the device of FIGS. 4 and 5;

FIG. 8 is a fragmentary view illustrating a guide assembly used in the device of FIGS. 4-7;

FIG. 9 illustrates one form of precut length of dental floss for use with the device of FIGS. 4-7; and FIGS. 10 and 11 illustrate two types of holders for holding or packaging a plurality of precut lengths of dental floss as illustrated in FIG. 9.

DESCRIPTION OF PREFERRED EMBODIMENTS

Figure 1:
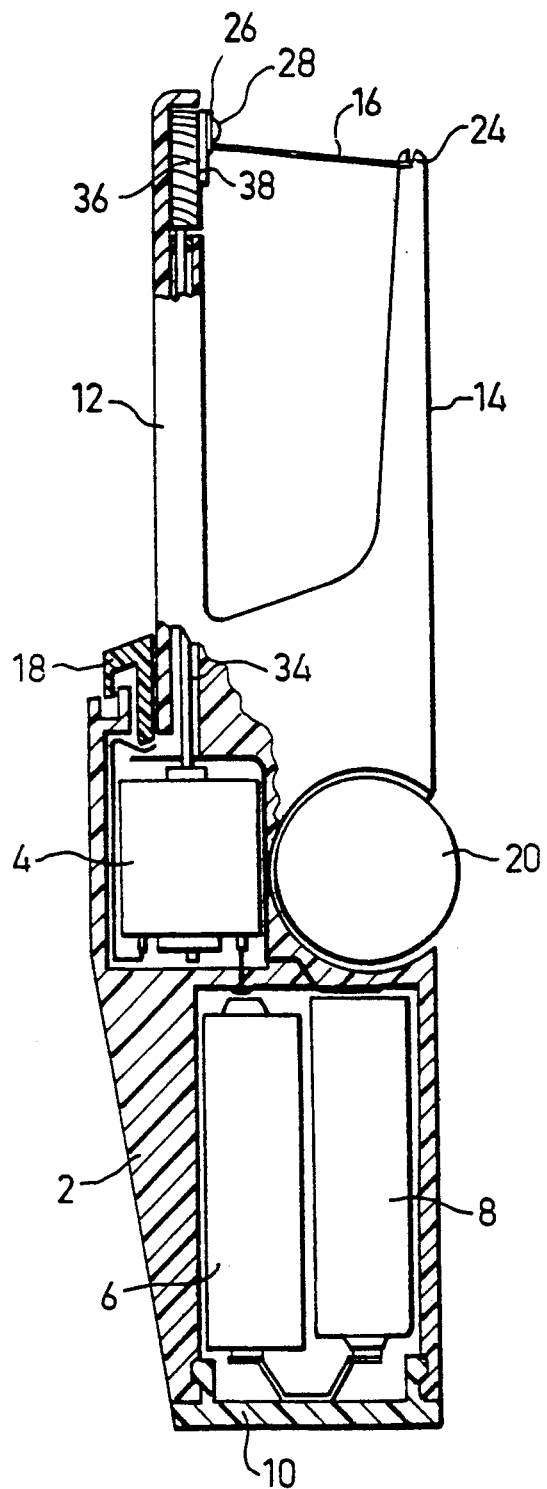
FIG. 1 is a longitudinal sectional view illustrating one form of dental flossing device constructed in accordance with the present invention.
Figure 2:
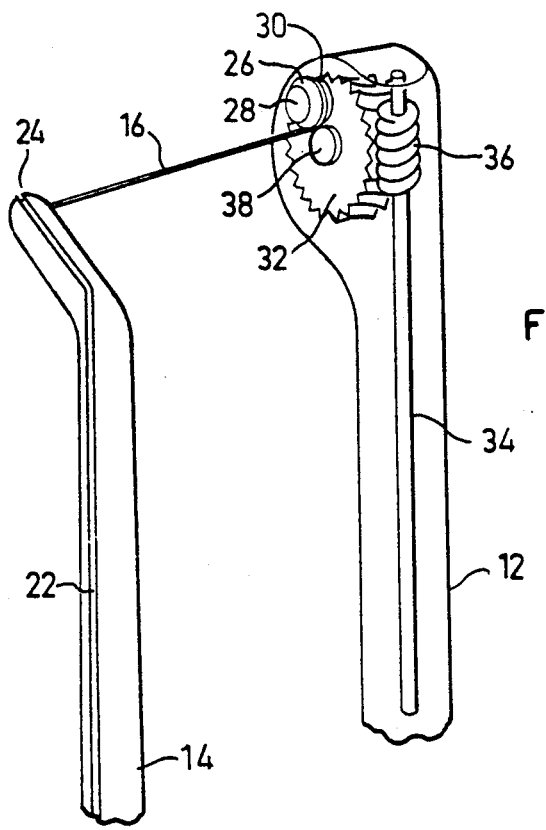
FIG. 2 is a perspective view more clearly illustrating the salient parts of the device of FIG. 1.

The Embodiment of FIGS. 1 and 2

The dental flossing device illustrated in FIGS. 1 and 2 comprises a housing 2 grippable by a user and including an electric motor 4 powered by a pair of batteries 6, 8 within the housing. One end of the housing is closed by a cover 10 to permit replacement of the batteries. A pair of arms 12, 14 project from the opposite end of the housing for securing between them a length of dental floss 16 to be oscillated by motor 4 as will be described more particularly below. The housing further includes an electrical switch 18 which is depressible to energize the motor.

The dental floss 16 is supplied from a cartridge 20 also carried by housing 2. The floss extends through a recess 22 (FIG. 2) along the length of arm 14, passes through a slot 24 formed in the outer tip of arm 14, and then is attached at its end to a roller 26 rotatably received on a pin 28 carried by arm 12. Any suitable attaching means may be used; in the construction illustrated in FIGS. 1 and 2, the attaching means comprises a rubber ring 30 seatable in a groove formed in roller 26.

Pin 28, securing one end of the length of dental floss 16 between the two arms 12, 14, is eccentrically located on a gear wheel 32 which is rotated by motor 4 via shaft 34 and worm gear 36. Gear wheel 32 thus serves as an eccentric which is rotatable about an axis defined by pin 38, which axis is substantially parallel to the axis of the length of the dental floss 16 extending between the two arms 12 and 14. When motor 4 is energized, the end of the dental floss 16 between the two arms is displaced by eccentric 32 through a planar unidirectional, curved, closed-loop path. This circular path follows that traversed by pin 28 on eccentric 32, and is defined by the two axes which are substantially perpendicular to each other and to the axis of the dental floss 16 between the two arms 12, 22.

Figure 2A:
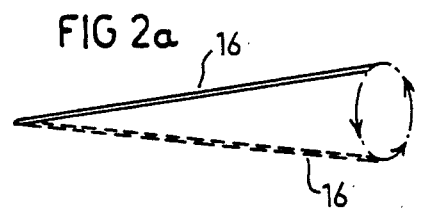
FIG. 2a is a diagram illustrating the planar circular path of oscillations of one end of the dental floss in the device of FIGS. 1 and 2.

This is more particularly illustrated in the diagram of FIG. 2a, wherein it will be seen that the end of the floss is displaced through the planar circular unidirectional, curved, closed-loop path illustrated by the arrows in FIG. 2a. It will be noted that these displacements of the floss end are confined to the plane of the two axes perpendicular to the floss; that is, the floss 16 is not oscillated or reciprocated along the axis parallel to its own length.

In use, the length of dental floss 16 would be inserted in between the user's teeth, preferably adjacent to the end secured to the eccentric 32 since the foregoing displacements would be of the largest magnitude at that end. These displacements of the dental floss effectively remove the deposits of dental plaque from between the teeth, while minimizing the "saw-like motion" which might damage the soft gingival tissue.

Figure 3:
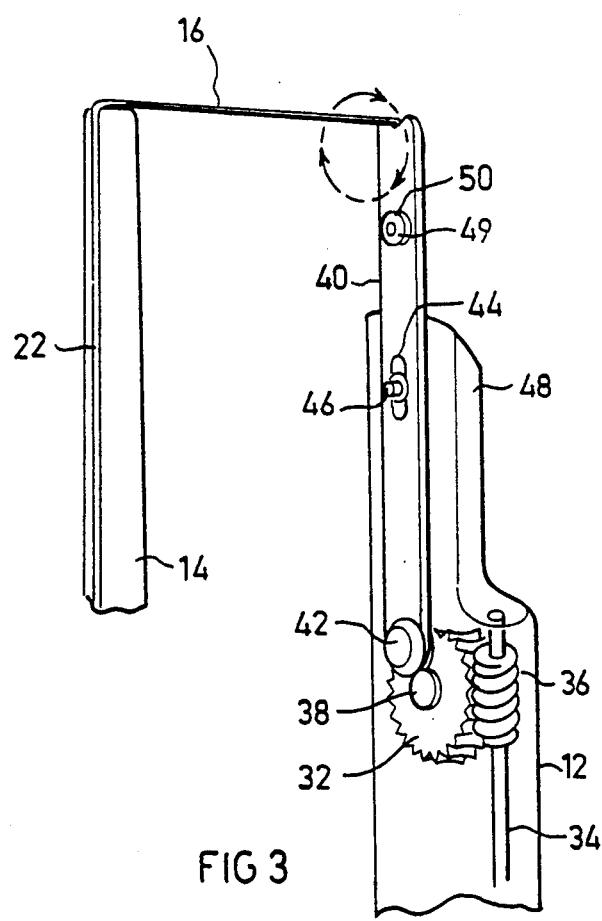
FIG. 3 is a perspective view illustrating a modification in the construction of the device of FIGS. 1 and 2.

The Variation of FIG. 3

FIG. 3 illustrates a variation in the construction of the device of FIGS. 1 and 2. In this variation, the end of the floss 16 passes over the upper end of a drive bar 40, the opposite end of the bar being pivotally coupled by pin 42 to the eccentric 32. Drive bar 40 is formed with an axial slot 44 receiving a pin 46 carried by an extension 48 of arm 12 to permit the bar both to pivot and to move axially with respect to arm 12. The end of the dental floss 16 is secured to bar 40 in any suitable manner, such as by means of the roller 48 and rubber ring 50.

The device illustrated by the variation in FIG. 3 is otherwise constructed, and operates in the same manner, as described above with respect to FIGS. 1 and 2. It will be seen that in this variation, the end of the dental floss 16 carried by arm 12 is also displaced through a unidirectional, curved, closed-loop planar path defined by the two axes substantially perpendicular to each other and to the dental floss axis (as illustrated in FIG. 2a), and thereby effectively clean the sides of the teeth, with no movement parallel to the axis of the dental floss which might possibly damage soft gingival tissue.

The Embodiment of FIGS. 4-9

FIGS. 4-8 illustrate a further dental flossing device constructed in accordance with the present invention. In this case, both ends of the dental floss are displaced through the unidirectional, curved, closed-loop planar path defined by the two axes substantially perpendicular to each other and to the dental floss axis; such a circular path is illustrated in FIG. 5a. In addition, the illustrated device permits precut lengths of dental floss, as illustrated in FIG. 9, to be applied to the device in a quick and simple manner.

Figure 4:
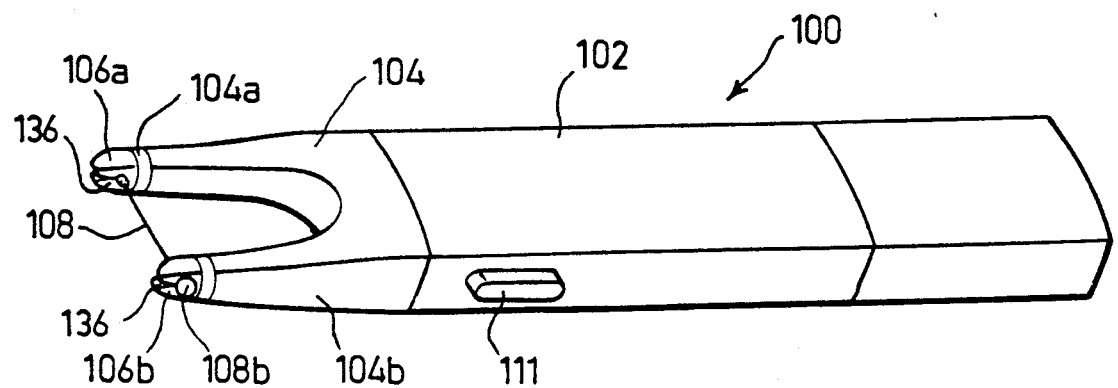
FIG. 4 illustrated another dental flossing device constructed in accordance with the invention.
Figure 6:
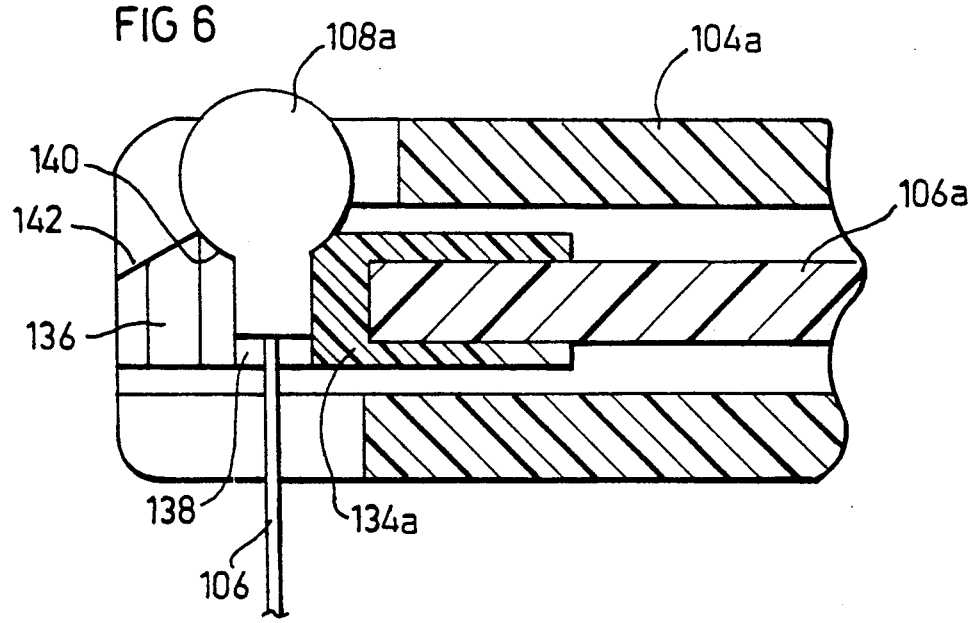
FIG. 6 is an enlarged sectional view illustrating a detail in the construction of the device of FIGS. 4 and 5.
Figure 7:
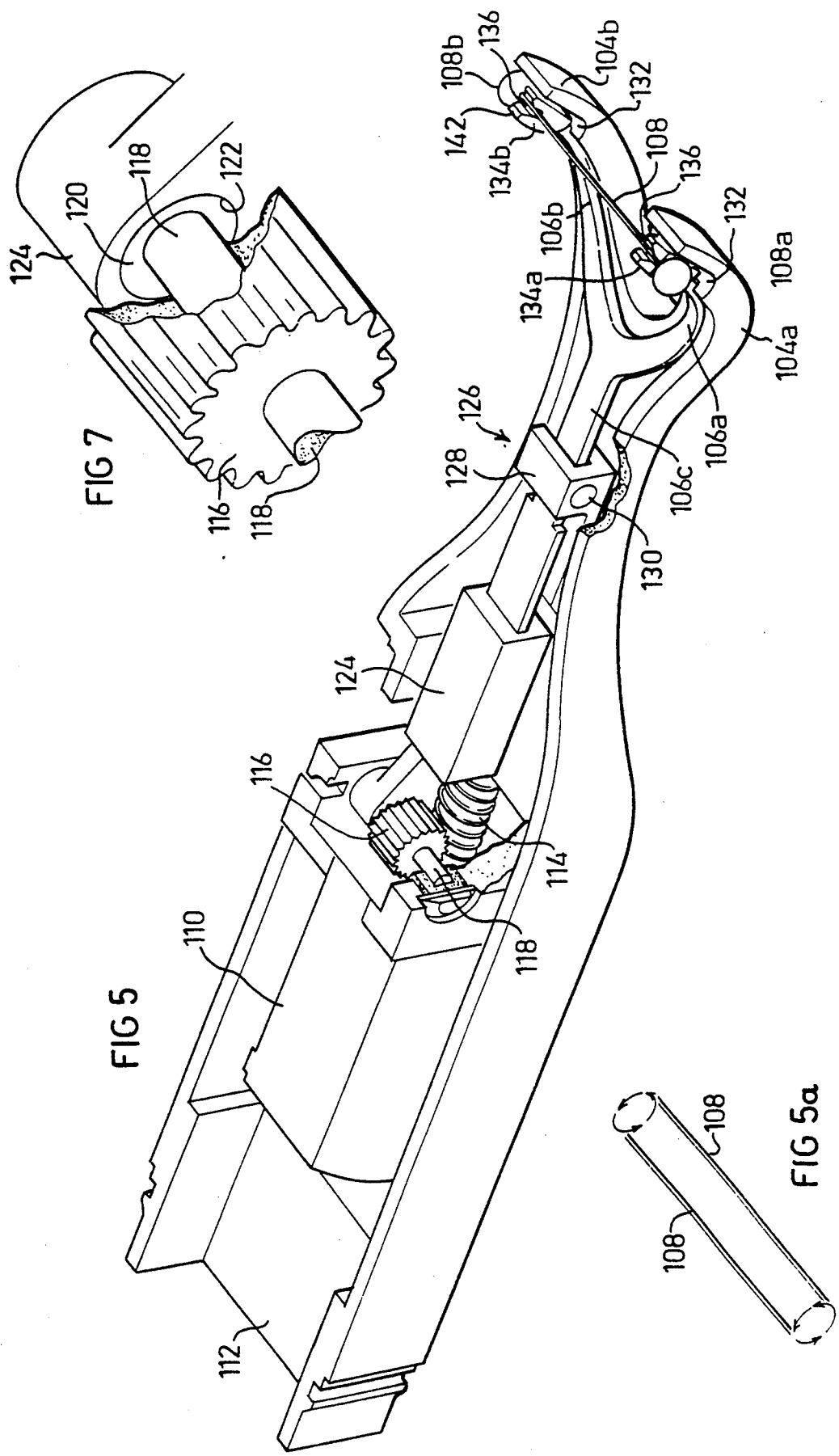
FIG. 7 is an enlarged fragmentary view illustrating the eccentric in the device of FIGS. 4 and 5.

The dental flossing device illustrated in FIGS. 4 and 5, and therein generally designated 100, comprises a housing 102 serving as a handle manually grippable by a user, and a bifurcated section 104 at one end covering a fork 106 (FIG. 5) disposed within the housing. Fork 106 is integrally formed with a pair of spaced arms 106a, 106b adapted to receive a dental floss unit 108. The dental floss unit 108, as more particularly illustrated in FIG. 9, consists of a precut length of dental floss terminating at its opposite ends in enlargements or spherical beads 108a, 108b. Fork 106 further includes a stem 106c extending inwardly of housing 102 and coupled to a drive for displacing the fork arms 106a, 106b and the floss unit 108 carried thereby.

The drive includes a rotary electrical motor 110 located within housing 102 and adapted to be energized under the control of a manual switch 111 by a pair of batteries (not shown) to be located within a battery compartment 112 in the housing. Motor 110 rotates a worm gear 114 meshing with a gear wheel 116. As shown particularly in FIG. 7, gear 116 has a shaft 118 which is eccentrically fixed to a cylindrical plug 120 rotatable within a cylindrical bore 122 formed in a coupling member 124. Coupling member 124 is fixed to the fork stem 106c so as to transmit its movements to the fork arms 106a, 106b, and thereby to the floss unit 108 carried by the arms.

It will be thus be seen that the cylindrical plug 120 constitutes an eccentric having a rotary axis (shaft 118) which is substantially parallel to the precut length of dental floss 108 carried by the fork arms 106a, 106b. Accordingly, as motor 110 rotates eccentric 120 (via worm gear 114 and gear wheel 166), the eccentric will displace the two fork arms 106a, 106b, and the floss unit 108 secured between them, through a unidirectional, curved, closed-loop path as illustrated in FIG. 5a, wherein the two ends, as well as each other point on the floss, moves through a unidirectional, curved, closed-loop planar path defined by the two axes substantially perpendicular to each other and to the dental floss axis, with no movement of the floss parallel to the floss axes.

The foregoing circular movement of fork 106, and the floss unit 108, is guided by a guide assembly 126 more particularly illustrated in FIG. 8. Guide assembly 126 includes an outer housing 128 and an inner bearing 130 terminating at its opposite ends in cylindrical surfaces 130a, 130b, and formed with a rectangular slot 130c receiving a reduced section of the fork stem 106c. Thus, the cylindrical ends 130a, 130b of bearing member 130 permit pivotal movement of the fork 106 about an axis (i.e., the axis extending transversely of the guide assembly housing 128) which is substantially parallel to the axis of the dental floss unit 108, whereas slot 130c permits slidable movement of the fork about an axis perpendicular to the dental floss axis.

As shown particularly in FIG. 5, housing section 104 includes two extensions 104a, 104b, around the two fork arms 106a, 106b. The two extensions are formed at their outer ends with a slot 132 for receiving the outer tips of the two fork arms. Slots 132 are dimensions to accommodate the displacements of the two arms.

The two fork arms 106a, 106b are made of an elastic material so as to be yieldable under force. A cap 134a, 134b is applied to the outer tip of each arm for receiving the dental floss unit 108. As shown particularly in FIG. 6, each cap (e.g., 134a, FIG. 6) is formed with an edge slot 136 extending from the outer tip of the cap inwardly for a short distance to a cylindrical bore 138 extending through the cap, and with a spherical recess 140 in the outer face of the cap. The outer surface of each cap is tapered, as shown at 142, to define a cam surface effective to cam the two arms inwardly towards each other when loading the device with a floss unit 108, as will be described more particularly below.

The Dental Floss Unit and Packaging Holder (FIGS. 9–11)

As described earlier, the dental flossing device illustrated in FIGS. 4–8 utilizes precut lengths of dental floss which may be quickly applied to the device. FIG. 9 illustrates one such dental floss unit which, as described above, terminates at its opposite ends in enlargements or spherical beads 108a, 108b; FIGS. 10 and 11 illustrate two forms of holders, generally designated 160 and 170, respectively, which may be used for holding and/or packaging a plurality of the floss units 108.

Thus, as shown in FIG. 10, holder 160 consists of a strip of plastic embossed with a line of straight, narrow recesses or cavities 162, each for receiving one of the floss units 108. The opposite ends of each straight line cavity 162 terminate in large cavities 162a, 162b of complementary spherical shape as the spherical beads 108a, 108b at the ends of the floss units 108, for receiving these beads. Each cavity 162a, 162b is formed with a plurality of radially-extending projections 164 engageable with the end beads 108a, 108b of the floss units 108 for releasably retaining them in the holder.

Holder 160 thus holds a plurality of floss units 108 in a compact and neatly packaged form. One end of the holder may be provided with an opening or slot 166 to permit displaying the package of floss units, as by suspension from a rack.

FIG. 11 illustrates another form of holder, generally designated 170, similarly formed with the straight cavities 172 for receiving the floss units 108. However, in this case the cavities 172a, 172b at the opposite ends of each straight cavity 172 are of rectangular, preferably square, configuration, rather than of circular configuration, to receive the bead enlargements 108a, 108b at the ends of each floss unit. While such beads are shown as of spherical configuration, it will be appreciated that they could be of other configurations, such as rectangular or square configuration. The enlarged cavities 172a–172b also include the radially-extending projections 174 for engaging the enlarged beads of the floss unit for releasably retaining the respective unit in the holder.

Loading and Operating the Device of FIGS. 4–8

The flossing tool illustrated in FIGS. 4–8 may be easily loaded with one of the floss units 108 (FIG. 9) directly from its holder 160 (FIG. 10) or 170 (FIG. 11) in the following manner:

The device is held vertically above one of the floss units 108, with the edge slots 136 in the caps 134a, 134b of the fork arms 106a, 106b aligned with the spherical cavities 162a, 162b in the holder 160 (or 172a, 172b in the holder of FIG. 11), and particularly with the cam surfaces 152 at the outer ends of the cap in alignment with the edges at the outer sides of the two enlarged cavities in the holder. The user then presses the device downwardly towards the holder 160, whereupon the edges of the outer sides of the cavities 162a, 162b (or 172a, 172b) in the holder engage the cam surfaces 152 of the caps 134a, 134b and force the fork arms 106a, 106b towards each other, until the spherical ends 108a, 108b snap into the spherical recesses 150 of the caps. The yieldable nature of the two fork arms 106a, 106b permit this convenient manner of loading a floss unit 108 onto the ends of the fork arms 106a, 106b.

Electrical switch 111 may then be operated to energize the electric motor 110. The motor rotates worm gear 114 to drive gear wheel 116, and thereby the eccentric plug 120 within the cylindrical cavity of the coupling member 124. This displaces the fork 106 such that each point on the floss unit 108 carried by the fork arms 106a, 106b passes through the unidirectional, curved, closed-loop planar path illustrated in FIG. 5a, namely the unidirectional, curved, closed-loop planar path defined by the two axes substantially perpendicular to each other and to the axis of the dental floss unit 1–8. As described earlier, such a movement of the dental floss unit effectively removes the dental plaque from between the teeth and at the same time avoids possible damage to the soft gingival tissues, since there is no movement of the floss unit parallel to its own longitudinal axis.

While the invention has been described with respect to several preferred embodiments, it will be appreciated that many other variations, modifications and applications of the invention may be made.

What is claimed is:

1. A dental flossing device, comprising:
   a housing manually grippable by a user;
   a pair of spaced arms projecting from one end of the housing and including floss-engaging means for engaging the opposite ends of a length of dental floss to be tautly secured along a dental floss axis between said arms;
   and a drive within said housing for displacing the length of dental floss when secured between said arms;
   characterized in that said drive displaces at least one end of the length of dental floss, when secured between the arms, through a unidirectional, curved, closed-loop planar path defined by the two axes substantially perpendicular to each other and to said dental floss axis.

2. The device according to claim 1, wherein said drive includes a rotary motor and an eccentric rotated by said motor along a rotary axis substantially parallel to said dental floss axis.

3. The device according to claim 2, wherein said drive further includes a worm gear rotated by the motor along an axis substantially perpendicular to said dental floss axis, said worm gear being coupled to a gear wheel secured to said eccentric to rotate it about an axis substantially parallel to said dental floss axis.

4. The device according to claim 1, wherein said drive displaces said floss-engaging means for one of said arms.

5. The device according to claim 1, wherein said drive displaces at least one of said arms.

6. The device according to claim 1, wherein said drive displaces both ends of the length of dental floss, when secured between the arms, through said planar circular path.

7. The device according to claim 6, wherein both of said arms are part of a fork, which fork is displaced by said drive through said planar circular path.

8. The device according to claim 7, wherein said drive includes a rotary motor rotating an eccentric about an axis parallel to said dental floss axis; said fork being coupled to said eccentric via guide means permitting pivotal movement of the fork about an axis substantially parallel to said dental floss axis, and slidable movement of the fork about an axis substantially perpendicular to said dental floss axis.

9. The device according to claim 7, wherein said pair of arms are yieldable and include edge slots at their outer tips to permit a precut length of dental floss having enlargements at its opposite ends to be quickly applied to the outer tips of the arms by forcing the outer tips of the arms towards each other when inserting the precut length of dental floss through said edge slots.

10. The device according to claim 9, wherein said outer tips of the arms are also formed with cam surfaces cooperable with surfaces formed in a holder for the precut length of dental floss, for forcing the outer tips of said arms towards each other when applying a precut length of dental floss thereto.

11. The device according to claim 7, wherein said housing includes a pair of extensions around said pair of arms but formed with slots receiving the outer tips of the arms and dimensioned to accommodate the displacements of the arms through said planar circular path.

12. A dental flossing device, comprising:
a housing manually grippable by a user;
a pair of spaced arms projecting from one end of the housing and including floss-engaging means for engaging the opposite ends of a length of dental floss to be tautly secured along a dental floss axis between said arms;
and a drive within said housing for displacing the length of dental floss when secured between said arms;
characterized in that said drive displaces each of said ends of the length of dental floss, when the dental floss is secured between the arms, through a unidirectional, curved, closed-loop planar path defined by the two axes substantially perpendicular to each other and to said dental floss axis.

13. The device according to claim 12, wherein said drive includes a rotary motor and an eccentric rotated by said motor along a rotary axis substantially parallel to said dental floss axis.

14. The device according to claim 13, wherein said drive further includes a worm gear rotated by the motor along an axis substantially perpendicular to said dental floss axis, said worm gear being coupled to a gear wheel secured to said eccentric to rotate it about an axis substantially parallel to said dental floss axis.

15. The device according to claim 12, wherein both of said arms are part of a fork, which fork is displaced by said drive through said planar circular path.

16. The device according to claim 15, wherein said drive includes a rotary motor rotating an eccentric about an axis parallel to said dental floss axis; said fork being coupled to said eccentric via guide means permitting pivotal movement of the fork about an axis substantially parallel to said dental floss axis, and slidable movement of the fork about an axis substantially perpendicular to said dental floss axis.

17. The device according to claim 15, wherein said pair of arms are yieldable and include edge slots at their outer tips to permit a precut length of dental floss having spherical beads at its opposite ends to be quickly applied to the outer tips of the arms by forcing the outer tips of the arms towards each other when inserting the precut length of dental floss through said edge slots.

18. The device according to claim 17, wherein said outer tips of the arms are also formed with cam surfaces cooperable with surfaces formed in a holder for the precut length of dental floss, for forcing the outer tips of said arms towards each other when applying a precut length of dental floss thereto.

19. The device according to claim 15, wherein said housing includes a pair of extensions around said pair of arms but formed with slots receiving the outer tips of the arms and dimensioned to accommodate the displacements of the arms through said planar circular path.

* * * * *